United States Patent
Bailey

(10) Patent No.: US 10,952,420 B2
(45) Date of Patent: Mar. 23, 2021

(54) FISHING SUGGESTIONS

(71) Applicant: Navico Holding AS, Egersund (NO)

(72) Inventor: Paul Robert Bailey, Auckland (NZ)

(73) Assignee: NAVICO HOLDING AS, Egersund (NO)

( * ) Notice: Subject to any disclaimer, the term of this patent is extended or adjusted under 35 U.S.C. 154(b) by 0 days.

(21) Appl. No.: 14/461,393

(22) Filed: Aug. 16, 2014

(65) Prior Publication Data

US 2015/0058323 A1 Feb. 26, 2015

Related U.S. Application Data

(60) Provisional application No. 61/868,444, filed on Aug. 21, 2013.

(51) Int. Cl.
*A01K 97/00* (2006.01)
*H04N 5/91* (2006.01)
(Continued)

(52) U.S. Cl.
CPC .............. *A01K 97/00* (2013.01); *A01K 79/00* (2013.01); *A01K 99/00* (2013.01); *A61B 5/1118* (2013.01); *A61B 5/1123* (2013.01); *G01B 21/00* (2013.01); *G01C 21/203* (2013.01); *G06F 3/014* (2013.01); *G06F 3/017* (2013.01); *G06F 3/0231* (2013.01); *G06F 3/0346* (2013.01); *G06F 11/3438* (2013.01); *G06F 11/3476* (2013.01); *G06F 15/0225* (2013.01); *G06F 16/9535* (2019.01); *G06K 9/00342* (2013.01);
(Continued)

(58) Field of Classification Search
CPC .......... G06F 17/3053; G06F 17/30867; G06Q 30/0269; H04N 21/25891; H04N 21/812
USPC ........................................................ 707/722
See application file for complete search history.

(56) References Cited

U.S. PATENT DOCUMENTS 4,751,787 A 6/1988 Jonsson
4,829,493 A 5/1989 Bailey
(Continued)

FOREIGN PATENT DOCUMENTS

DE 102004059619 A1 6/2006
EP 749687 A1 12/1996
(Continued)

OTHER PUBLICATIONS

PCT International Search Report and Written Opinion; PCT/IB2014/063979; dated Jan. 7, 2015.
(Continued)

*Primary Examiner* — Syed H Hasan
*Assistant Examiner* — Nicholas E Allen
(74) *Attorney, Agent, or Firm* — Nelson Mullins Riley & Scarborough LLP

(57) ABSTRACT

Various implementations described herein are directed to a non-transitory computer readable medium having stored thereon computer-executable instructions which, when executed by a computer, may cause the computer to receive a location, a date, a wind direction, a water temperature, a species, or combinations thereof. The computer may use the location, date, wind direction, water temperature, species, or combinations thereof to retrieve fishing data. The computer may analyze the retrieved fishing data to determine one or more suggested fishing locations.

12 Claims, 10 Drawing Sheets

(51) Int. Cl.
| | |
|---|---|
| *H04N 21/4335* | (2011.01) |
| *G06F 16/9535* | (2019.01) |
| *A01K 79/00* | (2006.01) |
| *G06F 11/34* | (2006.01) |
| *G06F 3/01* | (2006.01) |
| *G06K 9/00* | (2006.01) |
| *G11B 27/28* | (2006.01) |
| *G11B 27/34* | (2006.01) |
| *G06F 3/0346* | (2013.01) |
| *H04Q 9/00* | (2006.01) |
| *G01C 21/20* | (2006.01) |
| *G06T 7/246* | (2017.01) |
| *G06T 7/292* | (2017.01) |
| *G08C 17/02* | (2006.01) |
| *G06F 3/023* | (2006.01) |
| *G06F 15/02* | (2006.01) |
| *G06T 11/20* | (2006.01) |
| *G06T 7/60* | (2017.01) |
| *G11B 27/031* | (2006.01) |
| *G11B 27/17* | (2006.01) |
| *G11B 31/00* | (2006.01) |
| *A01K 99/00* | (2006.01) |
| *A61B 5/11* | (2006.01) |
| *G01B 21/00* | (2006.01) |
| *G06Q 10/00* | (2012.01) |
| *G06Q 50/00* | (2012.01) |
| *B63B 49/00* | (2006.01) |
| *G01S 15/96* | (2006.01) |
| *G06F 11/30* | (2006.01) |
| *G01S 7/00* | (2006.01) |

(52) U.S. Cl.
CPC ............ *G06Q 10/00* (2013.01); *G06Q 50/01* (2013.01); *G06T 7/246* (2017.01); *G06T 7/292* (2017.01); *G06T 7/60* (2013.01); *G06T 11/206* (2013.01); *G08C 17/02* (2013.01); *G11B 27/031* (2013.01); *G11B 27/17* (2013.01); *G11B 27/28* (2013.01); *G11B 27/34* (2013.01); *G11B 31/006* (2013.01); *H04N 5/91* (2013.01); *H04N 21/4335* (2013.01); *H04Q 9/00* (2013.01); *B63B 49/00* (2013.01); *G01S 7/003* (2013.01); *G01S 15/96* (2013.01); *G06F 11/3013* (2013.01); *G06F 11/3058* (2013.01); *G06F 2201/835* (2013.01); *G06T 2207/10016* (2013.01); *G06T 2207/30196* (2013.01); *G08C 2201/32* (2013.01); *H04Q 2209/43* (2013.01); *Y02D 10/00* (2018.01)

(56) References Cited

U.S. PATENT DOCUMENTS

| | | | |
|---|---|---|---|
| 4,879,697 A | 11/1989 | Lowrance et al. | |
| 5,025,423 A | 6/1991 | Earp | |
| 5,191,341 A | 3/1993 | Gouard et al. | |
| 5,228,228 A | 7/1993 | Meissner | |
| 5,321,391 A | 6/1994 | Fox | |
| 5,446,775 A | 8/1995 | Wright et al. | |
| 5,537,380 A | 7/1996 | Sprankle, Jr. et al. | |
| 5,546,695 A | 8/1996 | Langer | |
| 6,045,076 A | 4/2000 | Daniels | |
| 6,125,571 A | 10/2000 | Sigwald | |
| 6,222,449 B1 | 4/2001 | Twining | |
| 6,225,984 B1 | 5/2001 | Crawford | |
| 6,252,544 B1 | 6/2001 | Hoffberg | |
| 6,263,147 B1 | 7/2001 | Tognazzini | |
| 6,321,158 B1 | 11/2001 | DeLorme et al. | |
| 6,411,283 B1 | 6/2002 | Murphy | |
| 6,418,080 B2 | 7/2002 | Inouchi | |
| 6,421,299 B1 | 7/2002 | Betts et al. | |
| 6,459,372 B1 * | 10/2002 | Branham | A01K 97/00 340/539.1 |
| 6,567,792 B1 | 5/2003 | Arnold | |
| 6,584,722 B1 | 7/2003 | Walls | |
| 6,587,740 B2 | 7/2003 | Byrne et al. | |
| 6,751,626 B2 | 6/2004 | Brown et al. | |
| 6,761,692 B2 | 7/2004 | Angelsen et al. | |
| 6,798,378 B1 | 9/2004 | Walters | |
| 6,816,782 B1 | 11/2004 | Walters et al. | |
| 7,002,579 B2 | 2/2006 | Olson | |
| 7,236,426 B2 | 6/2007 | Turner et al. | |
| 7,243,457 B1 | 7/2007 | Smith et al. | |
| 7,319,992 B2 | 1/2008 | Gaos | |
| 7,321,824 B1 | 1/2008 | Nesbitt | |
| 7,430,461 B1 | 9/2008 | Michaels | |
| 7,652,952 B2 | 1/2010 | Betts et al. | |
| 7,669,360 B2 * | 3/2010 | Davidson | A01K 85/01 43/17 |
| 7,710,825 B2 | 5/2010 | Betts et al. | |
| 7,722,218 B2 | 5/2010 | Leung | |
| 7,729,203 B2 | 6/2010 | Betts et al. | |
| 7,755,974 B2 | 7/2010 | Betts et al. | |
| 7,812,667 B2 | 10/2010 | Fagg | |
| 7,870,496 B1 | 1/2011 | Sherwani | |
| 7,890,867 B1 | 2/2011 | Margulis | |
| 8,019,532 B2 | 9/2011 | Sheha et al. | |
| 8,040,758 B1 | 10/2011 | Dickinson | |
| 8,063,540 B2 | 11/2011 | Angelsen et al. | |
| 8,082,100 B2 | 12/2011 | Grace et al. | |
| 8,364,806 B2 | 1/2013 | Short et al. | |
| 8,452,797 B1 | 5/2013 | Paleja et al. | |
| 8,468,164 B1 | 6/2013 | Paleja et al. | |
| 8,512,238 B2 | 8/2013 | Nissilä et al. | |
| 8,721,453 B2 | 5/2014 | Rosing | |
| 9,439,411 B2 | 9/2016 | Bailey | |
| 9,507,562 B2 | 11/2016 | Bailey | |
| 9,572,335 B2 | 2/2017 | Bailey | |
| 9,615,562 B2 | 4/2017 | Bailey | |
| 2001/0054961 A1 | 12/2001 | Twining | |
| 2002/0035574 A1 | 3/2002 | Dumas | |
| 2002/0093541 A1 | 7/2002 | Schileru-Key | |
| 2002/0099457 A1 | 7/2002 | Fredlund et al. | |
| 2002/0116421 A1 | 8/2002 | Fox et al. | |
| 2003/0046689 A1 | 3/2003 | Gaos | |
| 2003/0056419 A1 * | 3/2003 | Squires | G06Q 10/10 43/4.5 |
| 2003/0089020 A1 | 5/2003 | Dirito | |
| 2003/0147981 A1 | 8/2003 | Gillam | |
| 2004/0124297 A1 | 7/2004 | Steer | |
| 2004/0162830 A1 | 8/2004 | Shirwadkar et al. | |
| 2004/0193364 A1 | 9/2004 | Chojnacki | |
| 2004/0198554 A1 | 10/2004 | On et al. | |
| 2004/0249860 A1 * | 12/2004 | Stechschulte | A01K 97/00 |
| 2005/0011105 A1 | 1/2005 | Cameron et al. | |
| 2005/0037872 A1 | 2/2005 | Fredlund et al. | |
| 2005/0102101 A1 | 5/2005 | Beesley et al. | |
| 2006/0013066 A1 | 1/2006 | Nishimori et al. | |
| 2006/0048434 A1 * | 3/2006 | Congel | A01K 97/00 43/4 |
| 2006/0053028 A1 * | 3/2006 | Congel | G06Q 30/00 705/1.1 |
| 2006/0095393 A1 * | 5/2006 | Vinsant | G09B 5/02 706/45 |
| 2006/0119585 A1 | 6/2006 | Skinner | |
| 2006/0224940 A1 | 10/2006 | Lee | |
| 2006/0265931 A1 | 11/2006 | McFadden et al. | |
| 2007/0011334 A1 | 1/2007 | Higgins et al. | |
| 2007/0045010 A1 | 3/2007 | Kasperek | |
| 2007/0058489 A1 | 3/2007 | Bratcher | |
| 2007/0220798 A1 | 9/2007 | Davidson | |
| 2008/0032666 A1 * | 2/2008 | Hughes | H04W 4/02 455/404.1 |
| 2008/0126935 A1 | 5/2008 | Blomgren | |
| 2008/0165022 A1 | 7/2008 | Herz et al. | |
| 2008/0204424 A1 | 8/2008 | Jin et al. | |
| 2008/0246627 A1 | 10/2008 | Guazzelli | |
| 2009/0064055 A1 | 3/2009 | Chaudhri et al. | |
| 2009/0099871 A1 | 4/2009 | Gadodia | |

(56) References Cited

U.S. PATENT DOCUMENTS

| | | |
|---|---|---|
| 2009/0105952 A1* | 4/2009 | Grace ............... G05D 1/0206 701/300 |
| 2009/0126254 A1* | 5/2009 | Yamazaki ............. A01K 79/00 43/4.5 |
| 2009/0179789 A1 | 7/2009 | Haughay, Jr. et al. |
| 2009/0231190 A1* | 9/2009 | Grumbles ............. G01C 21/00 342/357.57 |
| 2009/0240354 A1 | 9/2009 | Davidson |
| 2009/0241636 A1 | 10/2009 | Obori |
| 2009/0249247 A1 | 10/2009 | Tseng et al. |
| 2009/0258710 A1 | 10/2009 | Quatrochi |
| 2009/0271054 A1 | 10/2009 | Dokken |
| 2009/0287409 A1 | 11/2009 | Summers |
| 2009/0293336 A1* | 12/2009 | Lankinen ............. A01K 91/08 43/4 |
| 2009/0295626 A1 | 12/2009 | Su |
| 2010/0049468 A1 | 2/2010 | Papadourakis |
| 2010/0080082 A1 | 4/2010 | Betts et al. |
| 2010/0121716 A1 | 5/2010 | Golan |
| 2010/0145601 A1 | 6/2010 | Kurtti et al. |
| 2010/0198650 A1* | 8/2010 | Shaw ............... A01M 31/002 463/42 |
| 2010/0199225 A1 | 8/2010 | Coleman et al. |
| 2010/0226203 A1 | 9/2010 | Buttle et al. |
| 2010/0250122 A1 | 9/2010 | Kubota et al. |
| 2010/0295781 A1 | 11/2010 | Alameh et al. |
| 2010/0319235 A1 | 12/2010 | Panaro |
| 2011/0007035 A1 | 1/2011 | Shai |
| 2011/0013484 A1 | 1/2011 | Coleman et al. |
| 2011/0013485 A1 | 1/2011 | Maguire |
| 2011/0019887 A1 | 1/2011 | Roehrig et al. |
| 2011/0025720 A1 | 2/2011 | Jo et al. |
| 2011/0067290 A1 | 3/2011 | Miskatovic |
| 2011/0082644 A1 | 4/2011 | Imasaka et al. |
| 2011/0154183 A1 | 6/2011 | Burns et al. |
| 2011/0208479 A1* | 8/2011 | Chaves ............... A01K 97/00 702/187 |
| 2011/0213515 A1* | 9/2011 | Haymart ............. G01C 21/00 701/21 |
| 2011/0214500 A1 | 9/2011 | Cabrera et al. |
| 2011/0257819 A1 | 10/2011 | Chen et al. |
| 2012/0001773 A1 | 1/2012 | Lyons et al. |
| 2012/0010478 A1 | 1/2012 | Kinnunen et al. |
| 2012/0011437 A1 | 1/2012 | James et al. |
| 2012/0014220 A1* | 1/2012 | DePasqua ............. G01S 15/06 367/88 |
| 2012/0047790 A1 | 3/2012 | Hess et al. |
| 2012/0069712 A1 | 3/2012 | Potanin et al. |
| 2012/0095978 A1* | 4/2012 | Levin ............... G06F 17/30867 707/706 |
| 2012/0106300 A1 | 5/2012 | Maguire |
| 2012/0144384 A1 | 6/2012 | Baek |
| 2012/0144723 A1* | 6/2012 | Davidson ............. A01K 85/01 43/17.6 |
| 2012/0185801 A1 | 7/2012 | Madonna et al. |
| 2012/0253485 A1 | 10/2012 | Weast et al. |
| 2012/0293323 A1 | 11/2012 | Kaib et al. |
| 2012/0316456 A1 | 12/2012 | Rahman et al. |
| 2012/0316458 A1 | 12/2012 | Rahman et al. |
| 2012/0317167 A1 | 12/2012 | Rahman et al. |
| 2013/0007665 A1 | 1/2013 | Chaudhri et al. |
| 2013/0040714 A1 | 2/2013 | Rosing |
| 2013/0074051 A1 | 3/2013 | Freeman |
| 2013/0096575 A1 | 4/2013 | Olson |
| 2013/0107031 A1 | 5/2013 | Atkinson |
| 2013/0109997 A1 | 5/2013 | Linke et al. |
| 2013/0271301 A1 | 10/2013 | Kabel et al. |
| 2013/0281087 A1 | 10/2013 | Ruhanen et al. |
| 2013/0307720 A1* | 11/2013 | Lilburn ............... G01S 13/9035 342/25 F |
| 2013/0343151 A1 | 12/2013 | Shiraki et al. |
| 2014/0012587 A1 | 1/2014 | Park |
| 2014/0022864 A1* | 1/2014 | Lebedev ............. G01S 7/003 367/107 |
| 2014/0032468 A1 | 1/2014 | Anandaraj |
| 2014/0071059 A1 | 3/2014 | Girault |
| 2014/0111368 A1 | 4/2014 | Lee et al. |
| 2014/0135592 A1 | 5/2014 | Ohnemus et al. |
| 2014/0135631 A1 | 5/2014 | Brumback et al. |
| 2014/0164375 A1 | 6/2014 | Persson et al. |
| 2014/0180566 A1 | 6/2014 | Malhotra |
| 2014/0195297 A1 | 7/2014 | Abuelsaad et al. |
| 2014/0221854 A1 | 8/2014 | Wai |
| 2014/0358483 A1 | 12/2014 | da Rosa |
| 2015/0019135 A1 | 1/2015 | Kacyvenski |
| 2015/0051786 A1 | 2/2015 | Wang |
| 2015/0054655 A1 | 2/2015 | Bailey |
| 2015/0054732 A1 | 2/2015 | Bailey |
| 2015/0054828 A1 | 2/2015 | Bailey |
| 2015/0054829 A1 | 2/2015 | Bailey |
| 2015/0055827 A1 | 2/2015 | Bailey |
| 2015/0055930 A1 | 2/2015 | Bailey |
| 2015/0057929 A1 | 2/2015 | Bailey |
| 2015/0057965 A1 | 2/2015 | Gaynor |
| 2015/0057968 A1 | 2/2015 | Bailey |
| 2015/0058020 A1 | 2/2015 | Bailey |
| 2015/0058237 A1 | 2/2015 | Bailey |
| 2015/0058323 A1 | 2/2015 | Bailey |
| 2015/0245777 A1 | 9/2015 | Della Torre et al. |
| 2015/0310524 A1 | 10/2015 | Gospodarek et al. |
| 2015/0313199 A1* | 11/2015 | Castaneda ............. G01S 19/14 702/2 |
| 2015/0342481 A1 | 12/2015 | Lie et al. |
| 2016/0125348 A1 | 5/2016 | Dyer et al. |

FOREIGN PATENT DOCUMENTS

| | | |
|---|---|---|
| EP | 1 561 377 A1 | 8/2005 |
| EP | 1782687 | 5/2007 |
| EP | 2356902 A1 | 8/2011 |
| EP | 2 613 223 A1 | 7/2013 |
| GB | 2244195 A | 11/1991 |
| GB | 2426680 A | 12/2006 |
| GB | 2470904 | 12/2010 |
| JP | 2004 207812 A | 7/2004 |
| JP | 2006-158239 A | 6/2006 |
| JP | 2010 193284 A | 9/2010 |
| JP | 2011 139647 A | 7/2011 |
| WO | 1998/02037 A1 | 1/1998 |
| WO | 2004/088572 | 10/2004 |
| WO | 2010/056392 | 5/2010 |
| WO | WO 2012/059734 A1 | 5/2012 |
| WO | 2012/170163 | 12/2012 |
| WO | 2014088508 A1 | 6/2014 |
| ZA | 2003-08052 A | 7/2004 |

OTHER PUBLICATIONS

PCT International Search Report and Written Opinion; PCT/IB2014/063980; dated Jan. 5, 2015.

PCT International Search Report and Written Opinion; PCT/IB2014/063982; dated Dec. 22, 2014.

PCT International Search Report and Written Opinion; PCT/IB2014/063975; dated Dec. 3, 2014.

PCT International Search Report and Written Opinion; PCT/IB2014/063974; dated Dec. 2, 2014.

McElderry; At-Sea Observing Using Video-Based Electronic Monitoring; Prepared for: Electronic Monitoring Workshop Jul. 29-30, 2008; Archipelago Marine Research Ltd.

Office Action Issued in Canadian Patent Application 2,921,317, dated Feb. 7, 2017.

Allen, et al.; Upper Extremity Kinematic Trends of Fly-Casting; Establishing the Effects of Line Length; Sports Biomechanics; vol. 7, No. 1; Jan. 1, 2008; pp. 38-53.

First look at new Mio Link ANT +/Bluetooth Smart optical heart rate wrist band; http://www.dcrainmaker.com/2014/01/mio-link-first-look.html; Jan. 6, 2014 (accessed Apr. 19, 2016).

SAS, "SAS BI Dashboard 4.31 User's Guide", Second Edition, by SAS Electronic book, Aug. 1, 2012, downloaded at http://support.sas.com/documentation/cdl/en/bidbrdug/65580/PDF/default/bidrdrug.pdf.

(56) References Cited

OTHER PUBLICATIONS

PCT International Search Report and Written Opinion; PCT/IB2013/060285, dated Feb. 18, 2014; all enclosed pages cited.
PCT International Search Report and Written Opinion; PCT/IB2014/063976, dated Dec. 12, 2014; all enclosed pages cited.
PCT International Search Report and Written Opinion; PCT/IB2014/063983, dated Mar. 5, 2015; all enclosed pages cited.
PCT International Search Report and Written Opinion; PCT/US2013/047645, dated Sep. 27, 2013; all enclosed pages cited.
PCT International Search Report and Written Opinion; PCT/US2013/047869, dated Oct. 21, 2013; all enclosed pages cited.
PCT International Search Report and Written Opinion; PCT/US2013/047926, dated Oct. 11, 2013; all enclosed pages cited.
PCT International Search Report and Written Opinion; PCT/US2013/048129, dated Oct. 17, 2013; all enclosed pages cited.
PCT International Search Report and Written Opinion; PCT/US2013/048177, dated Oct. 21, 2013; all enclosed pages cited.
PCT International Search Report and Written Opinion; PCT/IB2014/063973, dated Nov. 28, 2014; all enclosed pages cited.
PCT International Search Report and Written Opinion; PCT/IB2014/063981, dated Feb. 10, 2015; all enclosed pages cited.
PCT International Search Report and Written Opinion; PCT/IB2014/063978, dated Dec. 19, 2014; all enclosed pages cited.
PCT International Search Report and Written Opinion; PCT/IB2014/063977, dated Nov. 28, 2014; all enclosed pages cited.

* cited by examiner

FISHING SUGGESTIONS

CROSS-REFERENCE TO RELATED APPLICATIONS

This application claims the benefit of U.S. Provisional Patent Application Ser. No. 61/868,444, filed Aug. 21, 2013 and titled FISHING DATA COLLECTION AND USE, the disclosure of which is incorporated herein by reference.

BACKGROUND

This section is intended to provide background information to facilitate a better understanding of various technologies described herein. As the section's title implies, this is a discussion of related art. That such art is related in no way implies that it is prior art. The related art may or may not be prior art. It should therefore be understood that the statements in this section are to be read in this light, and not as admissions of prior art.

Before and during a fishing trip, finding a good a location to fish may be a time consuming process for a fisherman. When determining where to fish, fisherman may consider a number of factors, such as past performance and present conditions. Fisherman often keep detailed logs of fishing performance and consult these logs when determining a location to fish. This process is time consuming, and may not effectively consider all of the available data.

SUMMARY

Described herein are implementations of various technologies for a method for analyzing fishing data to determine one or more suggested fishing locations. In one implementation, a non-transitory computer-readable medium having stored thereon computer-executable instructions which, when executed by a computer, cause the computer to perform various actions. The actions may include receiving a location, a date, a wind direction, a water temperature, a species, or combinations thereof. The actions may include using the location, date, wind direction, water temperature, species, or combinations thereof to retrieve fishing data. The actions may also include analyzing the retrieved fishing data to determine one or more suggested fishing locations.

Described herein are also implementations of various technologies for displaying a first map with a first set of one or more suggested fishing locations and displaying a second map with a second set of one or more suggested fishing locations. In one implementation, a non-transitory computer-readable medium having stored thereon computer-executable instructions which, when executed by a computer, cause the computer to perform various actions. The actions may include displaying a first map with a first set of one or more suggested fishing locations. The actions may include receiving a location, a date, a wind direction, a water temperature, a species, or combinations thereof. The actions may include using the location, date, wind direction, water temperature, species, or combinations thereof to determine a second set of one or more suggested fishing locations. The actions may also include displaying a second map with the second set of one or more suggested fishing locations.

Described herein are also implementations of various technologies for displaying expert suggestions on a map. In one implementation, a non-transitory computer-readable medium having stored thereon computer-executable instructions which, when executed by a computer, cause the computer to perform various actions. The actions may include receiving a location, a date, a wind direction, a water temperature, a species, or combinations thereof. The actions may include using the location, date, wind direction, water temperature, species or combinations thereof to retrieve expert suggestions. The actions may also include displaying the expert suggestions on a map.

The above referenced summary section is provided to introduce a selection of concepts in a simplified form that are further described below in the detailed description section. The summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

Implementations of various techniques will hereafter be described with reference to the accompanying drawings. It should be understood, however, that the accompanying drawings illustrate only the various implementations described herein and are not meant to limit the scope of various techniques described herein.

DETAILED DESCRIPTION

Figure 1:
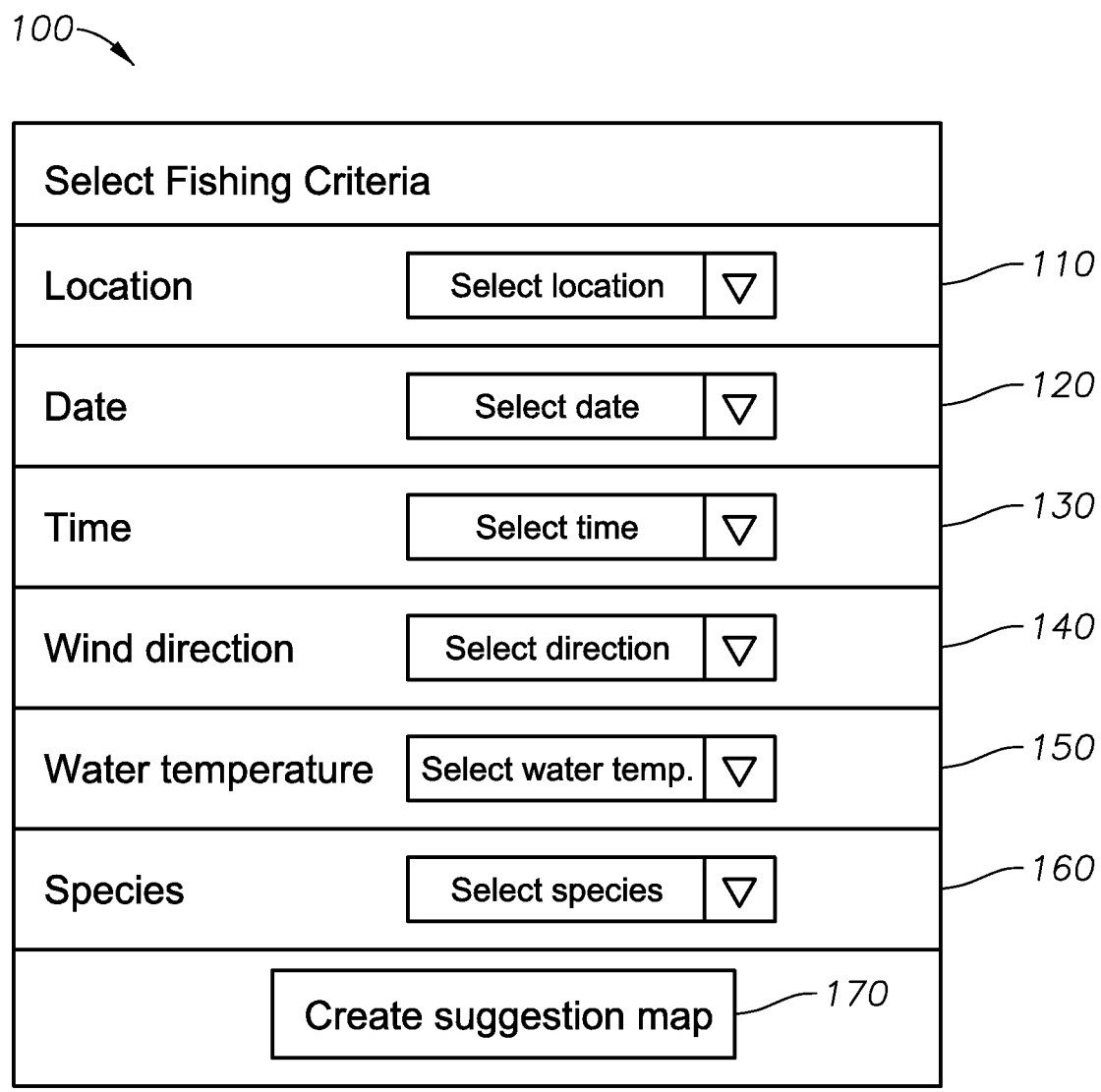
FIG. 1 illustrates a fishing criteria input interface in accordance with implementations of various techniques described herein.

The discussion below is directed to certain specific implementations. It is to be understood that the discussion below is only for the purpose of enabling a person with ordinary skill in the art to make and use any subject matter defined now or later by the patent "claims" found in any issued patent herein.

It is specifically intended that the claimed invention not be limited to the implementations and illustrations contained herein, but include modified forms of those implementations including portions of the implementations and combinations of elements of different implementations as come within the scope of the following claims. It should be appreciated that in the development of any such actual implementation, as in any engineering or design project, numerous implementation-specific decisions must be made to achieve the developers' specific goals, such as compliance with system-related and business related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure. Nothing in this application is considered critical or essential to the claimed invention unless explicitly indicated as being "critical" or "essential."

Reference will now be made in detail to various implementations, examples of which are illustrated in the accompanying drawings and figures. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first object or step could be termed a second object or step, and, similarly, a second object or step could be termed a first object or step, without departing from the scope of the invention. The first object or step, and the second object or step, are both objects or steps, respectively, but they are not to be considered the same object or step.

The terminology used in the description of the present disclosure herein is for the purpose of describing particular implementations only and is not intended to be limiting of the present disclosure. As used in the description of the present disclosure and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises" and/or "comprising," when used in this specification, specify the presence of stated features, integers, steps, operations, elements, and/or components, but do not preclude the presence or addition of one or more other features, integers, steps, operations, elements, components and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context. As used herein, the terms "up" and "down"; "upper" and "lower"; "upwardly" and "downwardly"; "below" and "above"; and other similar terms indicating relative positions above or below a given point or element may be used in connection with some implementations of various technologies described herein.

Various implementations of fishing suggestions described herein will now be described in more detail with reference to FIGS. 1-8.

FIG. 1 illustrates a fishing criteria input interface 100 in accordance with implementations of various techniques described herein. The interface 100 may be displayed by a cloud software service, on a smartphone, on a marine electronics device, such as the marine electronics device 800, described in FIG. 8, or on any other display device. The interface may be used to receive input for creating a fishing suggestion map. Examples of fishing suggestion maps are illustrated in FIGS. 2A-2D.

The interface 100 may be used to select various criteria in order to make fishing suggestions. A user may enter information for each criteria 110-160, or a subset of the criteria 110-160. At 110, a user may enter a location for fishing suggestions. For example, the location may be a body of water, latitude and longitude coordinates, or a path. At 120, a user may enter a date. The date may be an exact date, a time, a range of dates, or a season. At 130 a user may select tidal information. For example, a user may select outgoing tide or incoming tide. At 140, a user may select a wind direction and speed. At 150, a user may select a water temperature. At 160, a user may select one or more species of fish. After inputting criteria at one or more of 110-160, a user may select the create suggestion map button 170 to create a map of fishing suggestions.

Figure 2A:
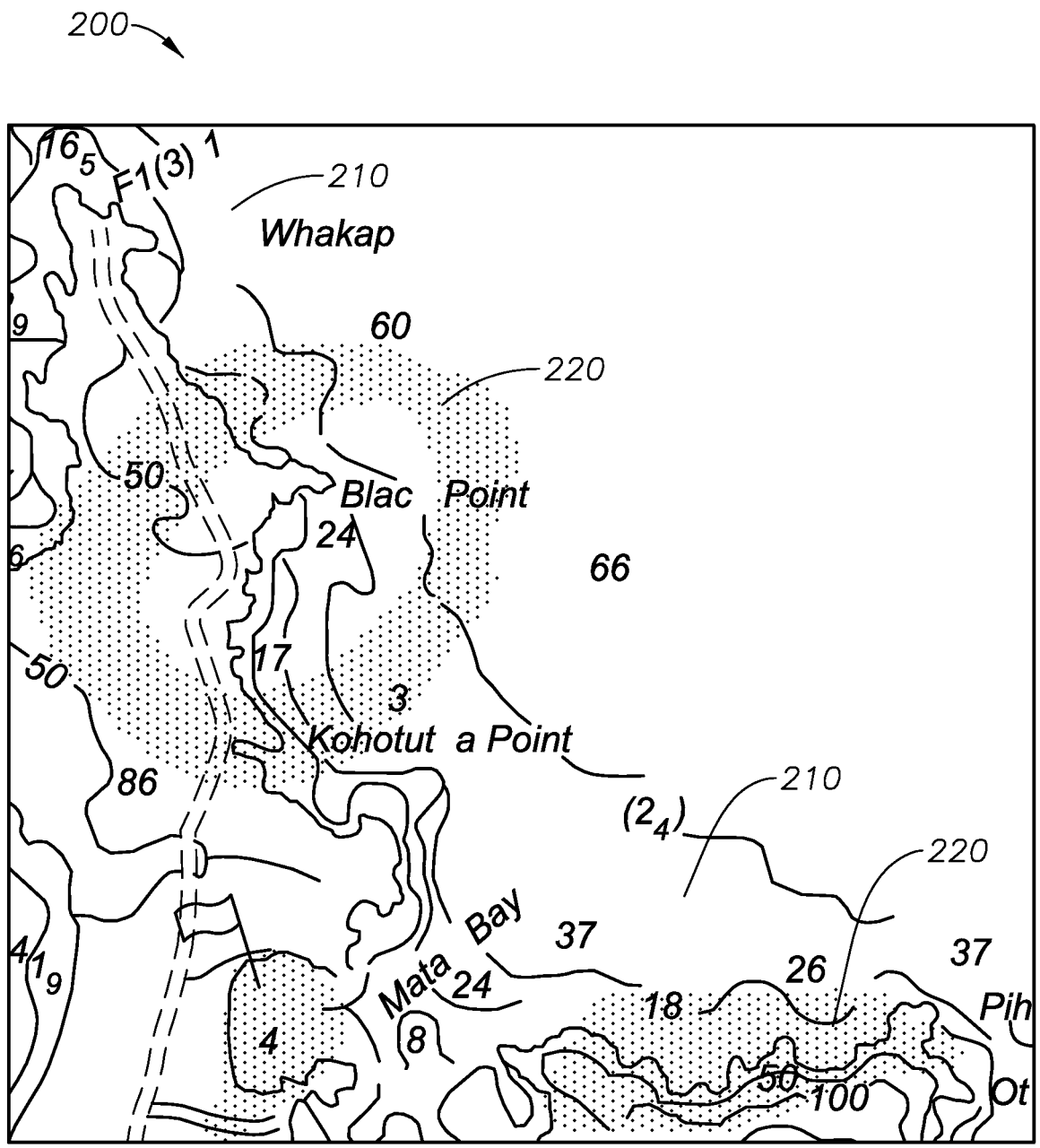
FIG. 2A illustrates a fishing suggestion display in accordance with various implementations described herein.

FIG. 2A illustrates a fishing suggestion display 200 in accordance with various implementations described herein. The fishing suggestion display 200 may be displayed on a marine electronics device as described in FIG. 8, a computer as described in FIG. 7, a smartphone device, or any other display device. The fishing suggestion display 200 may be generated by a cloud software service.

In the illustrated display 200, a map is shown with fishing suggestions 210 and 220. The patterned areas 220, which in this illustration are patterned with dots, are areas where fishing is highly suggested. The areas without a pattern 210 are areas where fishing is not as highly suggested. For example, if the fishing criteria is that a user wants to catch trout in an afternoon during the fall, areas 220 are areas where the user may be likely to catch trout during a fall afternoon, and areas 210 are areas where the user would be less likely to catch trout. Suggestions may be generated by method 400, described further in FIG. 4. Although the suggestions are displayed in the display 200 using patterns, any technique may be used to display the fishing suggestions. For example, numbers, colors or shading may be used to represent the fishing suggestions.

Figure 2B:
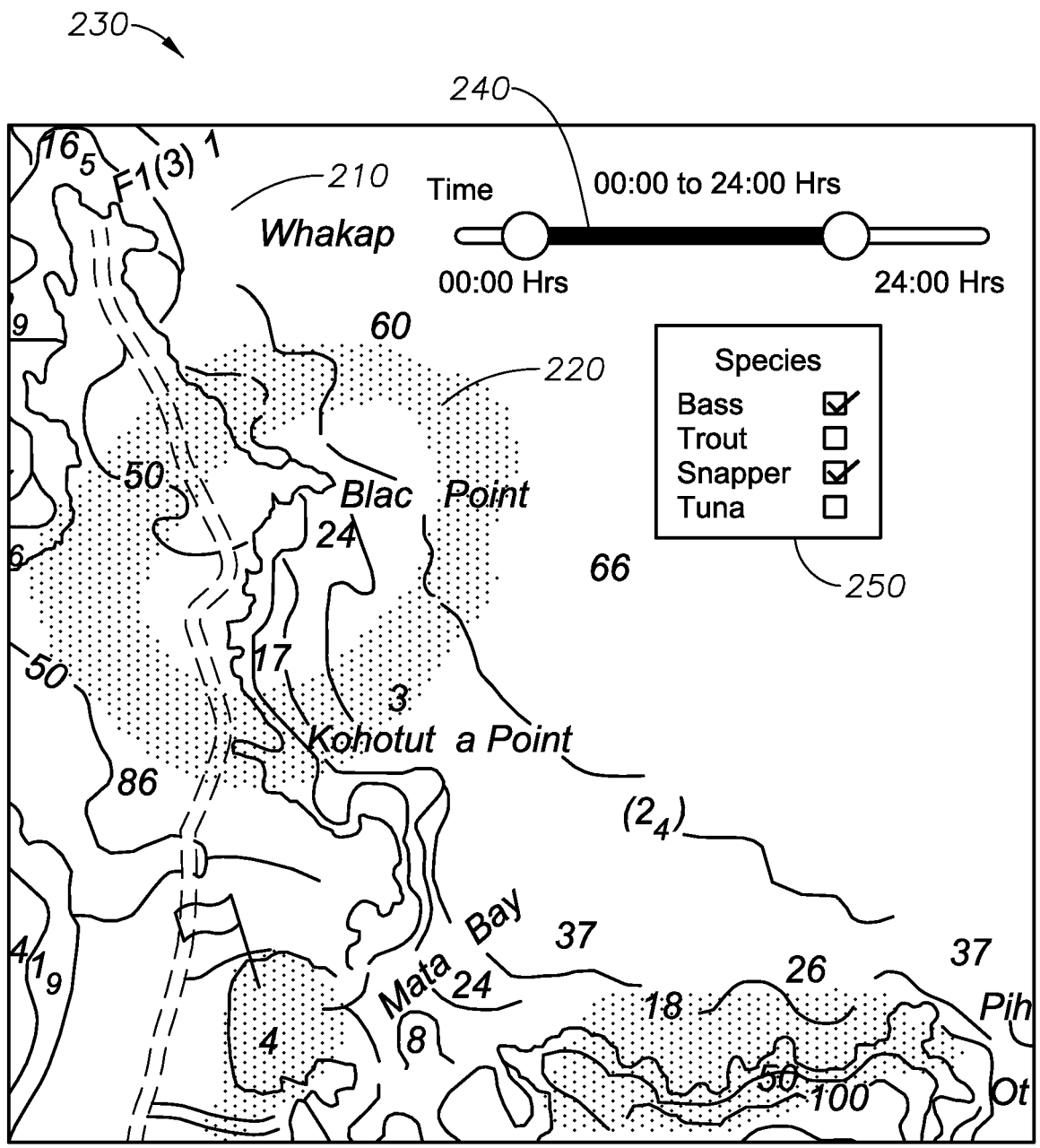
FIG. 2B illustrates a fishing suggestion display with selections in accordance with various implementations described herein.

FIG. 2B illustrates a fishing suggestion display 230 with selections in accordance with various implementations described herein. The fishing suggestion display 230 may be displayed on a marine electronics device as described in FIG. 8, a computer as described in FIG. 7, a smartphone device, or any other display device. The fishing suggestion display 230 may be generated by a cloud software service.

In the illustrated display 230, a map is shown with fishing suggestions 210 and 220. The criteria used to generate the suggestions 210 and 220 may be altered using slider 240 and selection box 250. Using the slider 240, a user may select a range of time for the suggestions in display 230. As the user alters the selection made using the slider 240, the displayed suggestions 210 and 220 may change in response to the selection. The selection box 250 may be used to select one or more species of fish that a user wants to catch. The suggestions 210 and 220 displayed on the map may change in response to the user's selections made using the selection box 250. Although time and species are shown as criteria that may be selected in the display 230, other criteria may be altered using a slider 240, selection box 250, or other input. For example, a user may be able to select a wind direction and speed by drawing an arrow on the map. In another example, the user may be able to select a location by selecting and dragging the map, or by zooming in or out.

Figure 2C:
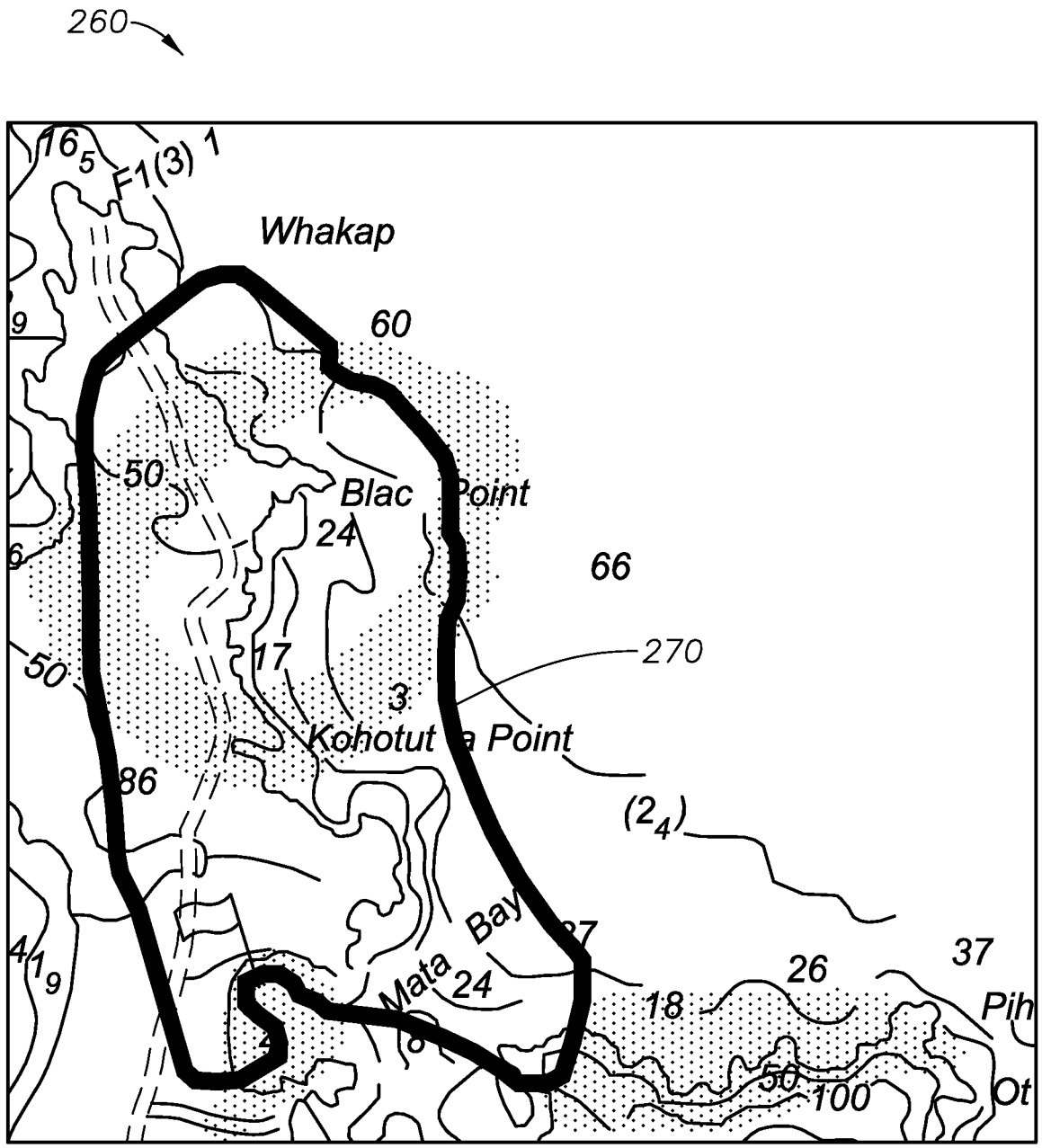
FIG. 2C illustrates a fishing suggestion and path display in accordance with various implementations described herein.

FIG. 2C illustrates a fishing suggestion and path display 260 in accordance with various implementations described herein. The fishing suggestion and path display 230 may be displayed on a marine electronics device as described in FIG. 8, a computer as described in FIG. 7, a smartphone device, or any other display device. The fishing suggestion and path display 230 may be generated by a cloud software service.

In the illustrated display 260, a map is shown with fishing suggestions and a path 270. The path 270 may be a recorded path. The path 270 may be a path traveled by a fisherman or vessel during a fishing trip. For example, during a fishing trip, a marine electronics device with a Global Positioning System (GPS) may be placed on a vessel to record location coordinates of the device. The location coordinates may then be saved as a path 270 and displayed on a display 260. In the display 260, a fisherman may be able to review fishing suggestions as well as a path 270 traveled during a prior fishing trip. In one implementation, the path 270 may be displayed during a fishing trip, and the path 270 may be locations traveled during the fishing trip.

Figure 2D:
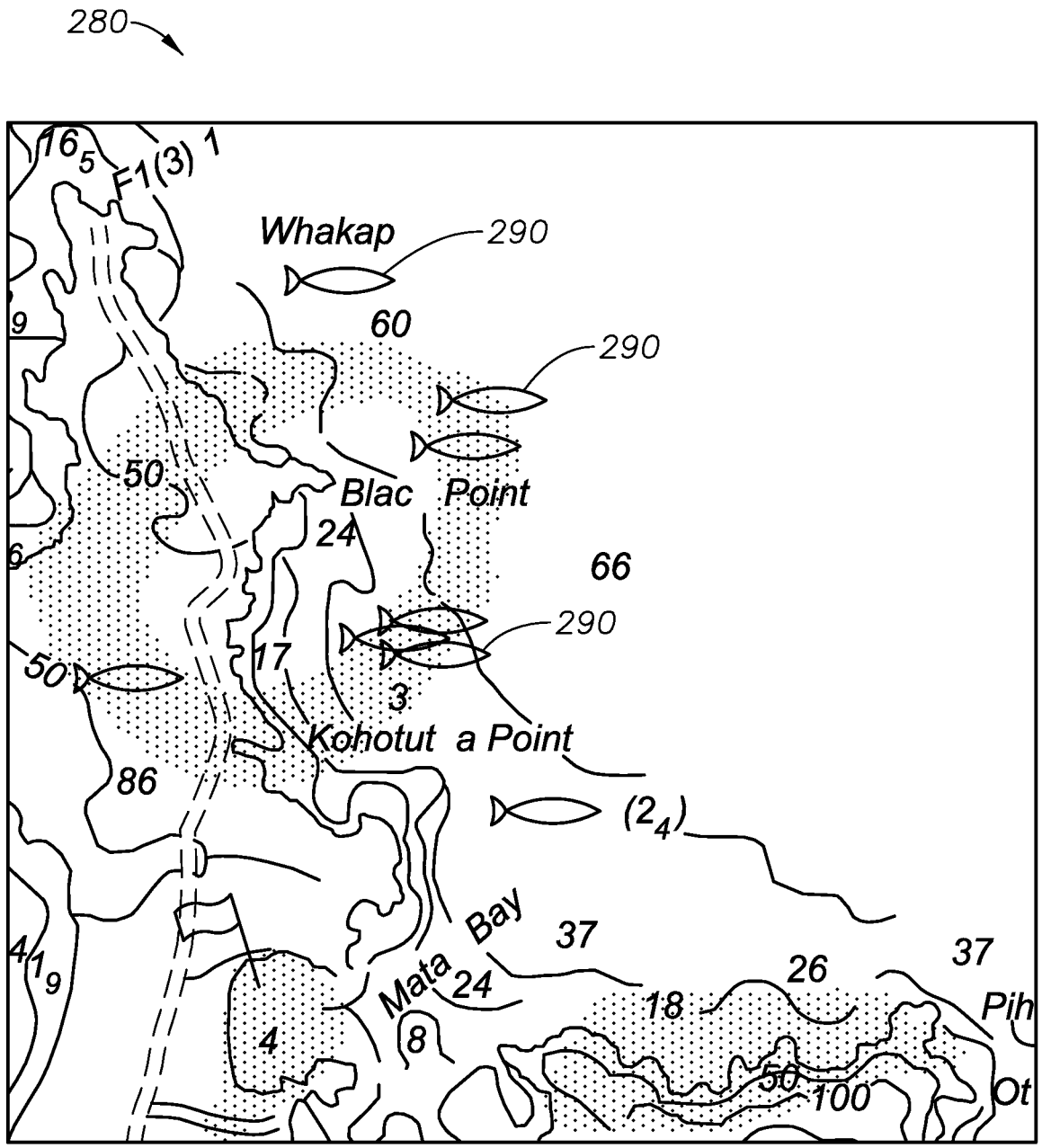
FIG. 2D illustrates a fishing suggestion and catch display in accordance with various implementations described herein.

FIG. 2D illustrates a fishing suggestion and catch display 280 in accordance with various implementations described herein. The fishing suggestion and catch display 280 may be displayed on a marine electronics device as described in FIG. 8, a computer as described in FIG. 7, a smartphone device, or any other display device. The fishing suggestion and catch display 280 may be generated by a cloud software service.

In the illustrated display 280, a map is shown with fishing suggestions and catch icons 290. The catch icons 290 may indicate locations where a fisherman has caught fish in the past. In the display 280, a fisherman may be able to view both recorded catches and fishing suggestions. The display may be used by a fisherman to compare locations where catches were recorded against suggested areas for fishing. Although the icons 290 in display 280 are in the shape of a fish and display the location of catches, any icon shape, colors or patterns may be used to display any event. For example, dots may be used to display the location of casts. In another example, stars may be used to display the location of waypoints.

Figure 3:
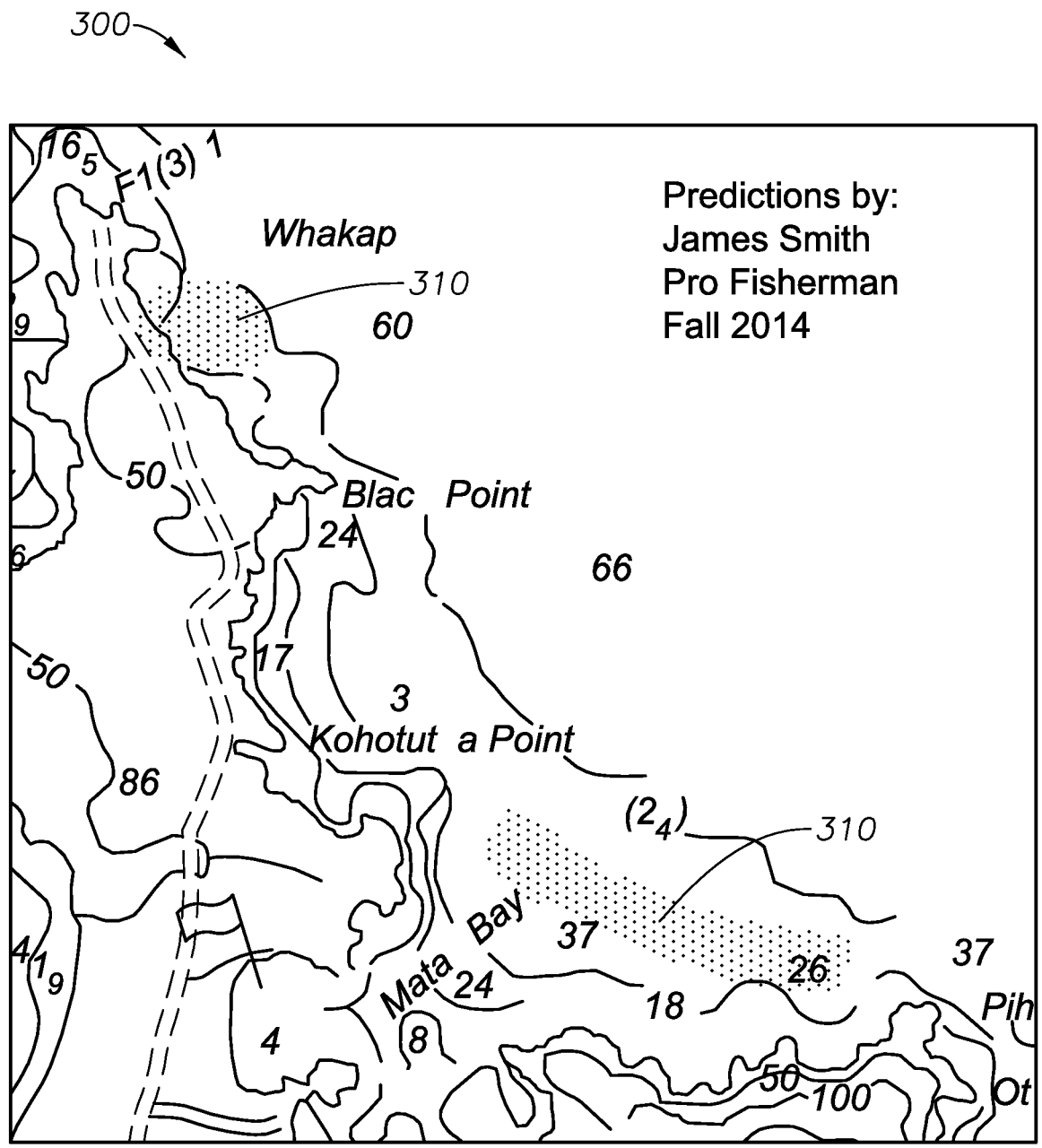
FIG. 3 illustrates an expert fishing suggestion display in accordance with various implementations described herein.

FIG. 3 illustrates an expert fishing suggestion display 300 in accordance with various implementations described herein. The expert fishing suggestion display 300 may be displayed on a marine electronics device as described in FIG. 8, a computer as described in FIG. 7, a smartphone device, or any other display device. The expert fishing suggestion display 300 may be generated by a cloud software service.

Display 300 includes expert suggestions 310. The expert suggestions 310 may indicate areas that an expert fisherman suggests for fishing. The suggestions display 300 may also display the credentials of the expert. In the display 300, the credentials indicate that the suggestions were made by a professional fisherman named James Smith, and that the suggestions are for the Fall of 2014.

The information displayed in displays 200, 230, 260, 280 and 300 may be displayed in any combination. For example, in one display, a map may include expert suggestions 310, catch icons 290 and a path 270.

Figure 4:
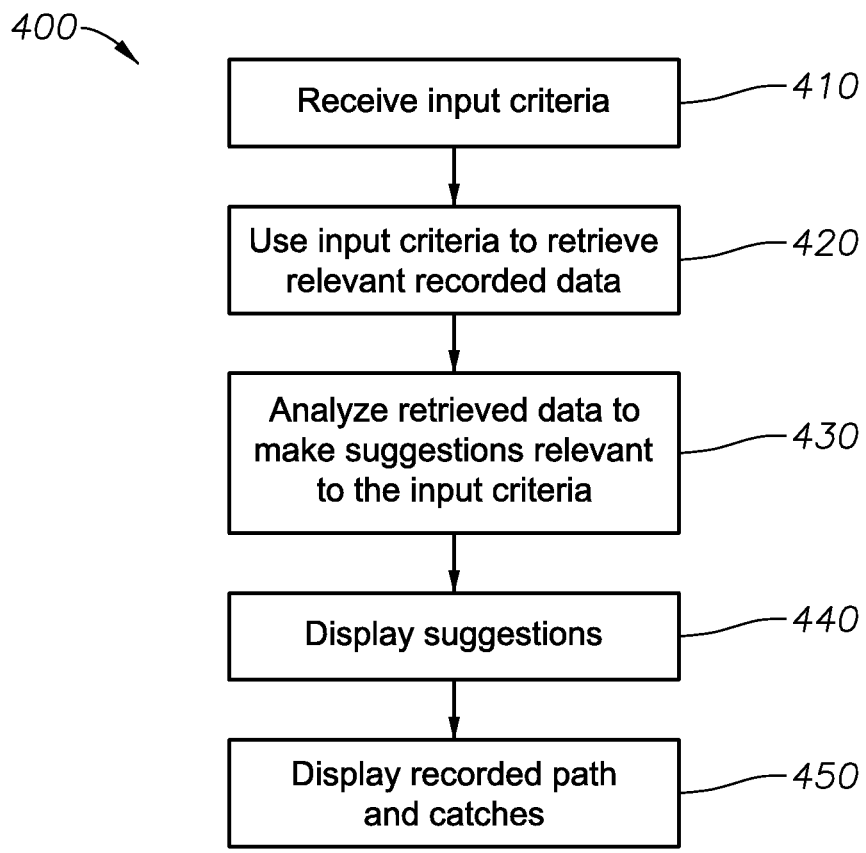
FIG. 4 is a flow diagram for a method of displaying fishing suggestions in accordance with implementations of various techniques described herein.

FIG. 4 is a flow diagram for a method 400 of displaying fishing suggestions in accordance with implementations of various techniques described herein. In one implementation, method 400 may be performed by any computer system 700, including a portable computer system, a smart phone device, a remote server, a marine electronics device 800, a cloud server and the like. It should be understood that while method 400 indicates a particular order of execution of operations, in some implementations, certain portions of the operations might be executed in a different order, and on different systems. Further, in some implementations, additional operations or steps may be added to the method 400. Likewise, some operations or steps may be omitted.

At block 410, method 400 may receive input criteria. The input criteria may be entered using an interface 100. The input criteria may include a location, date, tide, wind direction and strength, water temperature, or species. Other input criteria may be used as well. Input criteria may also be automatically determined. For example, if a time and date is entered, the tidal information may be automatically determined. In another example, when a fisherman is on the water, measurements, including temperature and location, may be recorded by a marine electronics device 800 and used as input criteria.

At block 420, method 400 may use the input criteria to retrieve relevant recorded data. The recorded data may be data recorded by one or more users. The recorded data may include information regarding casts, catches, bites, or other fishing events. The recorded data may include the location, time, environmental information, and other data related to the fishing events. The recorded data may include the path traveled by one or more fisherman during fishing trips. The recorded data may be stored, maintained, and retrieved by a cloud software service. Examples of data sources for the recorded data are explained in FIG. 6.

For example, if the input criteria received at block 410 includes a location that is a lake, at block 420 all recorded casts and catches that occurred on the lake may be retrieved. In another example, if the input criteria received at block 410 includes a tide, season, and species of fish, then method 400 may retrieve all catches of the species of fish that occurred during the selected season and when tidal conditions were similar to the selection.

At block 430, method 400 may analyze the data retrieved at block 420 in order to make suggestions relevant to the input criteria received at block 410. In one implementation, at block 430, the individual data points retrieved at block 420 may be weighted based on the input criteria, and then combined to form suggestions. For example, if a catch is recorded within the selected location when conditions were similar to the input criteria, then that catch would be weighted heavily, whereas if a catch occurred when conditions were not similar to the input criteria, the catch would not be weighted heavily.

In another implementation, where records of casts and catches are retrieved at block 420, method 400 may determine areas with a greater than average concentration of catches, or areas with a greater than average cast to catch ratio. For example, an area with a high cast to catch ratio in conditions similar to the input criteria may be suggested as a good area to fish.

In yet another implementation, the records of catches may be examined for patterns. For example, if a particular piece of equipment appears to be used frequently, method 400 may suggest using that piece of equipment. In another example, if a high cast to catch ratio occurs in certain conditions, method 400 may suggest fishing in those conditions.

At block 440, method 400 may display the suggestions. FIGS. 2A-2D illustrate examples of displays that may be created using method 400. The suggestions may be displayed on a computer system 700, marine electronics device 800, smart phone, or any other display device. The displayed suggestions may include one or more suggested locations for a fisherman to fish. For example, the suggestions may be displayed by shading the suggested areas on a map. In another example, the suggestions may be displayed by overlaying numbers on a map. In yet another example, the suggestions may be displayed by overlaying icons or text on the map. The displayed suggestions may include suggested equipment, suggested weather conditions, suggested times, suggested dates, suggested tidal conditions and the like.

At block 450, method 400 may display a recorded path, recorded catches, or both. This step is optional. Method 400 may also display any other recorded data, such as recorded bites, casts, sonar data, environmental data, or any other data. FIG. 2C illustrates a fishing suggestion display with a recorded path. FIG. 2D illustrates a fishing suggestion display with recorded catches. The recorded catches may be displayed by overlaying icons on the map. In one implementation, a user may select an icon, and further information regarding the selection will then be displayed. For example, a user may select an icon representing a caught fish, and information regarding the caught fish, such as time, date, species, equipment used, or environmental data may then be displayed.

Figure 5:
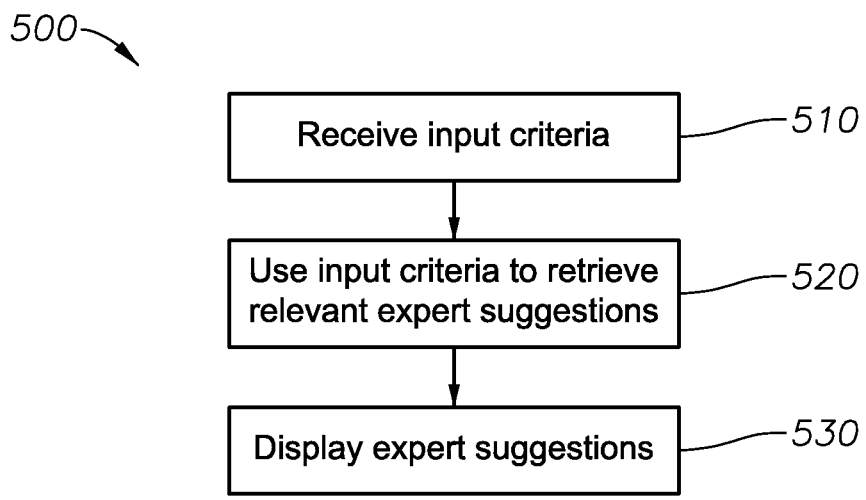
FIG. 5 is a flow diagram for a method of displaying expert fishing suggestions in accordance with implementations of various techniques described herein.

FIG. 5 is a flow diagram for a method 500 of displaying expert fishing suggestions in accordance with implementations of various techniques described herein. In one implementation, method 500 may be performed by any computer system 700, including a portable computer system, a smart phone device, a remote server, a marine electronics device 800, a cloud server and the like. It should be understood that while method 500 indicates a particular order of execution of operations, in some implementations, certain portions of the operations might be executed in a different order, and on different systems. Further, in some implementations, additional operations or steps may be added to the method 500. Likewise, some operations or steps may be omitted.

At block 510, method 500 may receive input criteria. The input criteria may be entered using an interface 100. The input criteria may include a location, date, tide, wind direction and strength, water temperature, species, or expert. Other input criteria may be used as well. Input criteria may also be automatically determined. For example, if a time and date is entered, the tidal information may be automatically determined. In another example, when a fisherman is on the water, measurements, including temperature and location, may be recorded by a marine electronics device 800 and used as input criteria. In one implementation, the input criteria is an expert and a location. In a second implementation, a user may first select a location as the input criteria, and a list of experts who have made suggestions near the location may then be displayed, the user may then select one of the experts in the list of experts as input criteria.

At block 520, method 500 may use the input criteria received at block 510 to retrieve relevant expert suggestions. For example if the input criteria is a location, at block 520, all expert suggestion near the location may be retrieved. In another example, if the input criteria is a species of fish, expert suggestions from experts who specialize in catching the species of fish may be retrieved.

At block 530, method 500 may display the expert suggestions retrieved at block 520. FIG. 3 is an example of an expert suggestion display. The display may include suggestions from one or more experts. The display may allow the user to alter the input criteria. For example, a user may be able to zoom in or out to change the location used to retrieve relevant expert suggestions. In another example, the user may be able to select different experts to view different expert suggestions.

Figure 6:
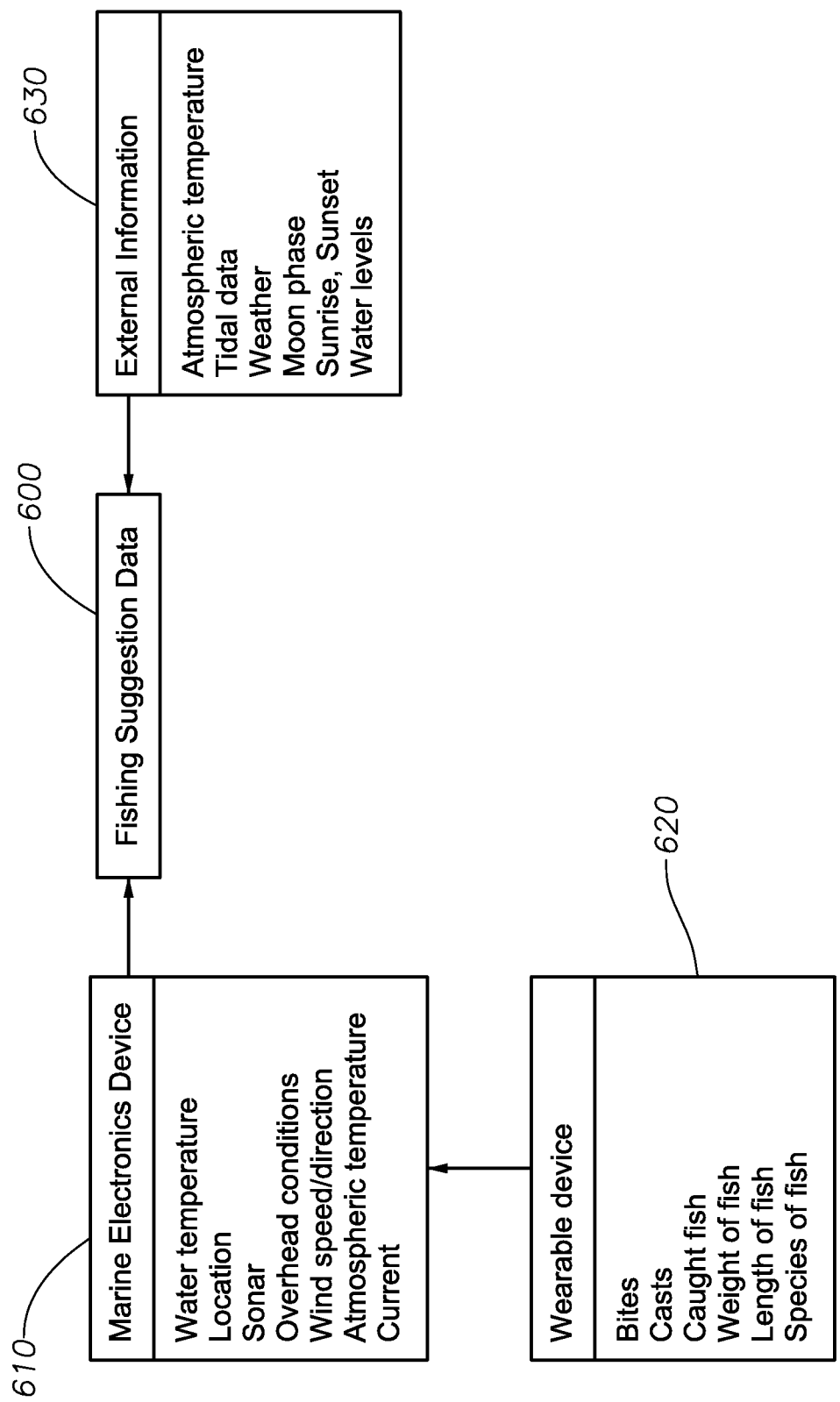
FIG. 6 is a diagram of fishing data sources in accordance with implementations of various techniques described herein.

FIG. 6 is a diagram of fishing data sources in accordance with implementations of various techniques described herein. Fishing suggestions data 600 may be used to generate fishing suggestions. In one implementation, the fishing suggestions data 600 is stored using a database. Data from various sources may be transferred to a cloud software service, stored in the database, and used as fishing suggestion data 600. Fishing suggestion data 600 may be located on a computer system 700. Fishing suggestion data 600 may be stored on any device capable of collecting and storing fishing data, including a marine electronics device 800 or a smart phone device. Fishing suggestion data 600 may comprise data collected by one or more fishermen. For example, fishing suggestion data 600 may comprise data collected by a plurality of users of a cloud software service.

A wearable device 620 may be used to collect fishing statistics such as bites, casts, caught fish, the weight of a caught fish, the length of a caught fish, and other fishing statistics. The statistics may be automatically collected by a wearable device 620 with motion sensors. The fishing statistics collected using wearable device 620 may be transmitted to a marine electronics device 610, or directly to a database storing fishing suggestion data 600. The marine electronics device 610 is described in more detail with reference to FIG. 8.

The marine electronics device 610 may collect fishing statistics such as water temperature, location, sonar, overhead conditions, wind speed and direction, atmospheric temperature, current, and other fishing statistics. This information may be transmitted directly to a database, or may be transmitted to another device, such as a smart phone, and then transmitted to a database.

External information 630 may also be retrieved and stored in a database. The external information 630 may be retrieved from the Internet or any other source by a computer system 700. The external information 630 may include atmospheric temperature, tidal data, weather, moon phase, sunrise, sunset, water levels, or any other fishing data.

Computing System

Implementations of various technologies described herein may be operational with numerous general purpose or special purpose computing system environments or configurations. Examples of well known computing systems, environments, and/or configurations that may be suitable for use with the various technologies described herein include, but are not limited to, personal computers, server computers, hand-held or laptop devices, multiprocessor systems, microprocessor-based systems, set top boxes, programmable consumer electronics, network PCs, minicomputers, mainframe computers, smart phones, tablets, wearable computers, cloud computing systems, virtual computers, marine electronics devices, and the like.

The various technologies described herein may be implemented in the general context of computer-executable instructions, such as program modules, being executed by a computer. Generally, program modules include routines, programs, objects, components, data structures, etc. that performs particular tasks or implement particular abstract data types. Further, each program module may be implemented in its own way, and all need not be implemented the same way. While program modules may all execute on a single computing system, it should be appreciated that, in some implementations, program modules may be implemented on separate computing systems or devices adapted to communicate with one another. A program module may also be some combination of hardware and software where particular tasks performed by the program module may be done either through hardware, software, or both.

The various technologies described herein may be implemented in the context of marine electronics, such as devices found in marine vessels and/or navigation systems. Ship instruments and equipment may be connected to the computing systems described herein for executing one or more navigation technologies. As such, the computing systems may be configured to operate using sonar, radar, GPS and like technologies.

The various technologies described herein may also be implemented in distributed computing environments where tasks are performed by remote processing devices that are linked through a communications network, e.g., by hardwired links, wireless links, or combinations thereof. In a distributed computing environment, program modules may be located in both local and remote computer storage media including memory storage devices.

Figure 7:
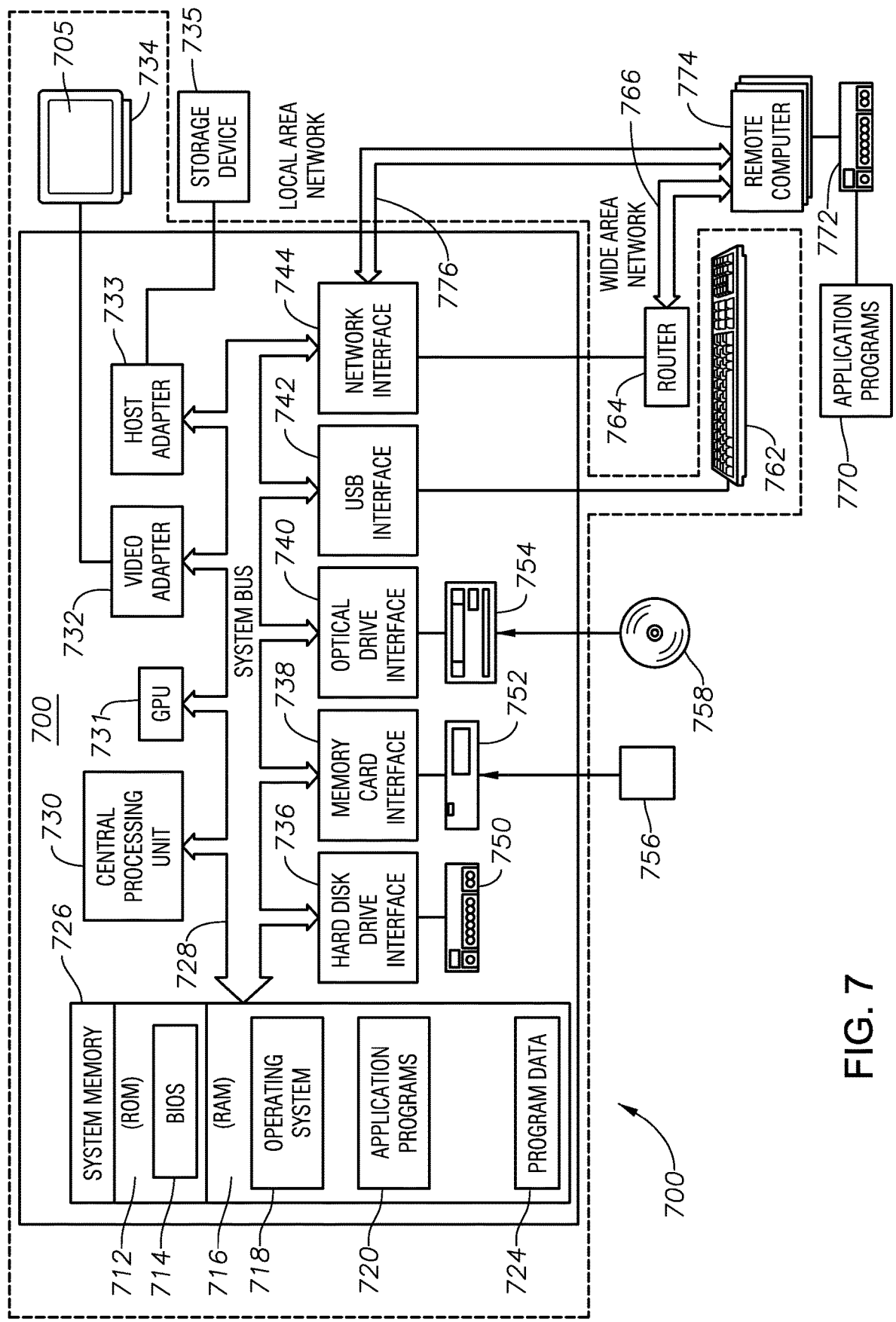
FIG. 7 illustrates a schematic diagram of a computing system in which the various technologies described herein may be incorporated and practiced.

FIG. 7 illustrates a computer system 700 into which implementations of various technologies and techniques described herein may be implemented. Computing system 700 may be a conventional desktop, a handheld device, a wearable device, a controller, a personal digital assistant, a server computer, an electronic device/instrument, a laptop, a tablet, or part of a navigation system, marine electronics, or sonar system. It should be noted, however, that other computer system configurations may be used.

The computing system 700 may include a central processing unit (CPU) 730, a system memory 726 and a system bus 728 that couples various system components including the system memory 726 to the CPU 730. Although only one CPU 730 is illustrated in FIG. 7, it should be understood that in some implementations the computing system 700 may include more than one CPU 730.

The CPU 730 can include a microprocessor, a microcontroller, a processor, a programmable integrated circuit, or a combination thereof. The CPU 730 can comprise an off-the-shelf processor such as a Reduced Instruction Set Computer (RISC), including an Advanced RISC Machine (ARM) processor, or a Microprocessor without Interlocked Pipeline Stages (MIPS) processor, or a combination thereof. The CPU 730 may also include a proprietary processor. The CPU may include a multi-core processor.

The CPU 730 may provide output data to a Graphics Processing Unit (GPU) 731. The GPU 731 may generate graphical user interfaces that present the output data. The GPU 731 may also provide objects, such as menus, in the graphical user interface. A user may provide inputs by interacting with the objects. The GPU 731 may receive the inputs from interaction with the objects and provide the inputs to the CPU 730. In one implementation, the CPU 730 may perform the tasks of the GPU 731. A video adapter 732 may be provided to convert graphical data into signals for a monitor 734. The monitor 734 includes a screen 705. The screen 705 can be sensitive to heat or touching (now collectively referred to as a "touch screen"). In one implementation, the computer system 700 may not include a monitor 734.

The GPU 731 may be a microprocessor specifically designed to manipulate and implement computer graphics. The CPU 730 may offload work to the GPU 731. The GPU 731 may have its own graphics memory, and/or may have access to a portion of the system memory 726. As with the CPU 730, the GPU 731 may include one or more processing units, and each processing unit may include one or more cores.

The system bus 728 may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. The system memory 726 may include a read only memory (ROM) 712 and a random access memory (RAM) 716. A basic input/output system (BIOS) 714, containing the basic routines that help transfer information between elements within the computing system 700, such as during start-up, may be stored in the ROM 712. The computing system may be implemented using a printed circuit board containing various components including processing units, data storage memory, and connectors.

Certain implementations may be configured to be connected to a GPS and/or a sonar system. The GPS and/or sonar system may be connected via the network interface 744 or Universal Serial Bus (USB) interface 742. In one implementation, the computing system 700, the monitor 734, the screen 705 and buttons may be integrated into a console.

The computing system 700 may further include a hard disk drive 736 for reading from and writing to a hard disk 750, a memory card reader 752 for reading from and writing to a removable memory card 756 and an optical disk drive 754 for reading from and writing to a removable optical disk 758, such as a CD ROM, DVD ROM or other optical media. The hard disk drive 750, the memory card reader 752 and the optical disk drive 754 may be connected to the system bus 728 by a hard disk drive interface 736, a memory card interface 738 and an optical drive interface 740, respectively. The drives and their associated computer-readable media may provide nonvolatile storage of computer-readable instructions, data structures, program modules and other data for the computing system 700.

Although the computing system 700 is described herein as having a hard disk 750, a removable memory card 756 and a removable optical disk 758, it should be appreciated by those skilled in the art that the computing system 700 may also include other types of computer-readable media that may be accessed by a computer. For example, such computer-readable media may include computer storage media and communication media. Computer storage media may include volatile and non-volatile, and removable and non-removable media implemented in any method or technology for storage of information, such as computer-readable instructions, data structures, program modules or other data. Computer storage media may further include RAM, ROM, erasable programmable read-only memory (EPROM), electrically erasable programmable read-only memory (EEPROM), flash memory or other solid state memory technology, including a Solid State Disk (SSD), CD-ROM, digital versatile disks (DVD), or other optical storage, magnetic cassettes, magnetic tape, magnetic disk storage or other magnetic storage devices, or any other medium which can be used to store the desired information and which can be accessed by the computing system 700. Communication media may embody computer readable instructions, data structures, program modules or other data in a modulated data signal, such as a carrier wave or other transport mechanism and may include any information delivery media. By way of example, and not limitation, communication media may include wired media such as a wired network or direct-wired connection, and wireless media such as acoustic, RF, infrared and other wireless media. The computing system 700 may also include a host adapter 733 that connects to a storage device 735 via a small computer system interface (SCSI) bus, a Fiber Channel bus, an eSATA bus, or using any other applicable computer bus interface. The computing system 700 can also be connected to a router 764 to establish a wide area network (WAN) 766 with one or more remote computers 774. The router 764 may be connected to the system bus 728 via a network interface 744. The remote computers 774 can also include hard disks 772 that store application programs 770.

In another implementation, the computing system 700 may also connect to one or more remote computers 774 via local area network (LAN) 776 or the WAN 766. When using a LAN networking environment, the computing system 700 may be connected to the LAN 776 through the network interface or adapter 744. The LAN 776 may be implemented via a wired connection or a wireless connection. The LAN 776 may be implemented using Wi-Fi technology, cellular technology, or any other implementation known to those skilled in the art. The network interface 744 may also utilize remote access technologies (e.g., Remote Access Service (RAS), Virtual Private Networking (VPN), Secure Socket Layer (SSL), Layer 2 Tunneling (L2T), or any other suitable protocol). These remote access technologies may be implemented in connection with the remote computers 774. It will be appreciated that the network connections shown are exemplary and other means of establishing a communications link between the computer systems may be used. The network interface 744 may also include digital cellular networks, Bluetooth, or any other wireless network interface.

A number of program modules may be stored on the hard disk 750, memory card 756, optical disk 758, ROM 712 or RAM 716, including an operating system 718, one or more application programs 720, program data 724 and a database system. The one or more application programs 720 may contain program instructions configured to perform methods 400 or 500 according to various implementations described herein. The operating system 718 may be any suitable operating system that may control the operation of a networked personal or server computer, such as Windows® XP, Mac OS® X, Unix-variants (e.g., Linux® and BSD®), Android®, iOS®, and the like.

A user may enter commands and information into the computing system 700 through input devices such as a keyboard 762 and pointing device. Other input devices may include a microphone, joystick, game pad, satellite dish, scanner, user input button, wearable device, or the like. These and other input devices may be connected to the CPU 730 through a USB interface 742 coupled to system bus 728, but may be connected by other interfaces, such as a parallel port, Bluetooth or a game port. A monitor 705 or other type of display device may also be connected to system bus 728 via an interface, such as a video adapter 732. In addition to the monitor 734, the computing system 700 may further include other peripheral output devices such as speakers and printers.

Marine Electronics Device

Figure 8:
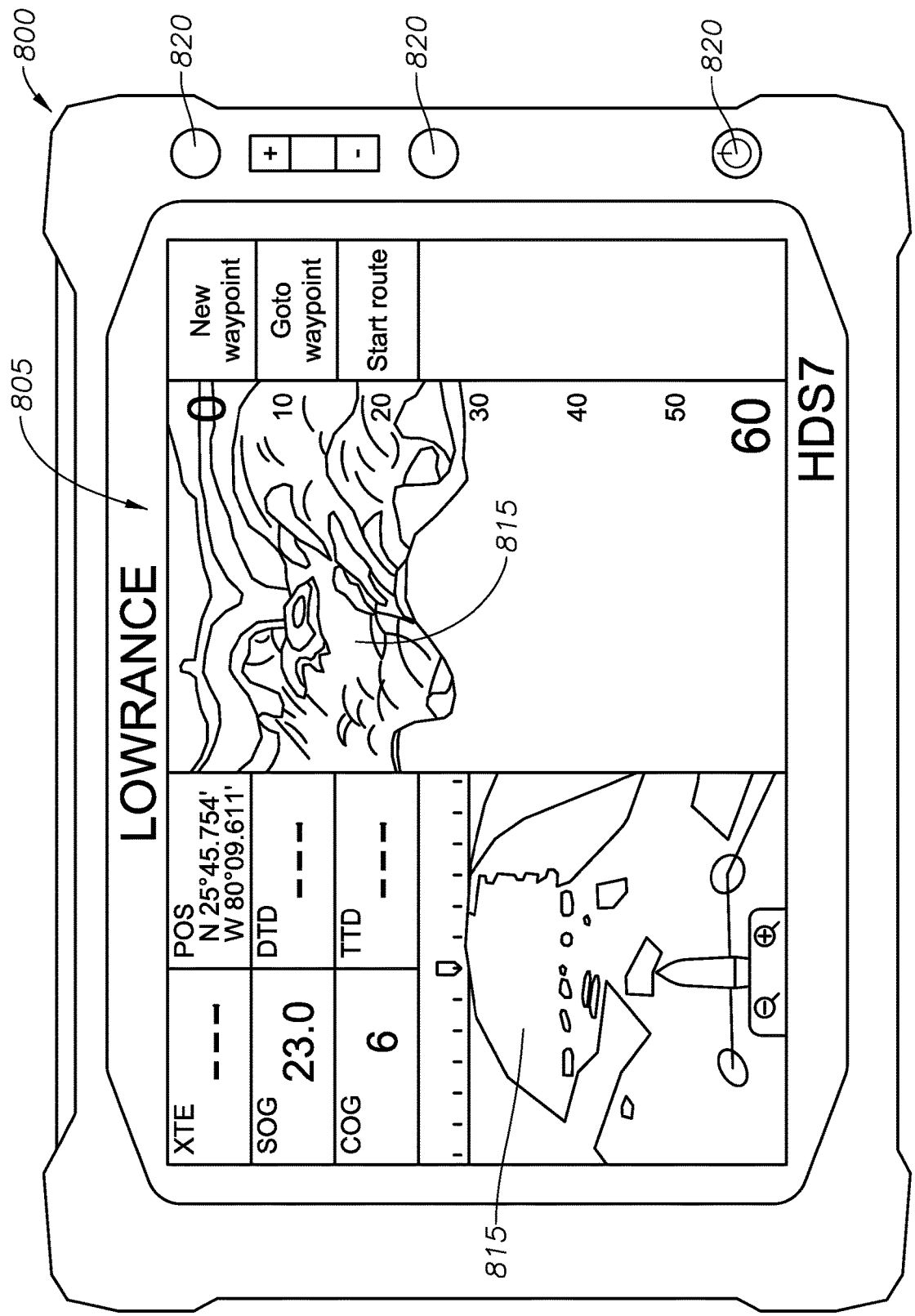
FIG. 8 illustrates a schematic of a marine electronics device in accordance with implementations of various techniques described herein.

FIG. 8 illustrates a schematic diagram of a marine electronics device 800 in accordance with various implementations described herein. The marine electronics device 800 includes a screen 805. In certain implementations, the screen 805 may be sensitive to touching by a finger. In other implementations, the screen 805 may be sensitive to the body heat from the finger, a stylus, or responsive to a mouse. The device 800 may display marine electronic data 815. The marine electronic data types 815 may include chart data, radar data, sonar data, steering data, dashboard data, navigation data, fishing data, and the like. The marine electronics device 800 may also include a plurality of buttons 820, which may be either physical buttons or virtual buttons, or a combination thereof. The marine electronics device 800 may receive input through a screen 805 sensitive to touch or buttons 820. The marine electronics device 800 may be connected to a motion capture device using a wired connection, such as USB, or through a wireless connection, such as Bluetooth.

While the foregoing is directed to implementations of various techniques described herein, other and further implementations may be devised without departing from the basic scope thereof, which may be determined by the claims that follow.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A non-transitory computer-readable medium having stored thereon a plurality of computer-executable instructions which, when executed by a computer, cause the computer to:

receive, at a marine electronics device of a marine vessel, one or more environmental measurements during a fishing trip, wherein the one or more environmental measurements comprise at least one of a location of the marine vessel or a water temperature;

determine input criteria comprising at least one of a location, a date, a wind direction, a water temperature, or a species, wherein at least a portion of the input criteria is determined automatically without user input and based on the received one or more environmental measurements;

retrieve fishing data relevant to the input criteria from a database, wherein the fishing data comprises fishing records from a plurality of users;

analyze the retrieved fishing data to determine one or more suggested fishing locations based on the input criteria;

retrieve one or more suggestions relevant to the input criteria, wherein the one or more suggestions comprise one or more areas suggested for fishing; and display, on a screen of the marine electronics device, the suggestions on a map such that the one or more areas suggested for fishing are highlighted on the map with respect to remaining areas on the map using at least one of a plurality of repeated-patterned dots, one or more colors, or shading that cover an entirety of each of the one or more areas suggested for fishing.

2. The non-transitory computer-readable medium of claim 1, wherein the location is a body of water and wherein the suggested fishing locations are in the same body of water as the location.

3. The non-transitory computer-readable medium of claim 1, wherein the computer-executable instructions further cause the computer to:
   receive a distance, and
      wherein the suggested fishing locations are within the distance of the location.

4. The non-transitory computer-readable medium of claim 1, wherein the fishing records comprise records of casts, catches, or combinations thereof.

5. The non-transitory computer-readable medium of claim 4, wherein the records of casts include at least one of locations, dates, wind directions, water temperatures, equipment used, or types of casts.

6. The non-transitory computer-readable medium of claim 4, wherein the records of catches include at least one of locations, dates, wind directions, water temperatures, species, length, or weight.

7. The non-transitory computer-readable medium of claim 1, wherein the instructions that cause the computer to display the suggestions on the map comprise instructions that cause the computer to darken the one or more areas suggested for fishing on the map.

8. The non-transitory computer-readable medium of claim 4, wherein the instructions that cause the computer to analyze the retrieved data to determine one or more suggested fishing locations comprise instructions that cause the computer to weight the records of casts and catches.

9. The non-transitory computer-readable medium of claim 1, wherein the instructions that cause the computer to analyze the retrieved data to determine one or more suggested fishing locations comprise instructions that cause the computer to determine areas with a greater than average amount of catches or greater than average cast to catch ratio.

10. The non-transitory computer-readable medium of claim 1, wherein the computer-executable instructions further cause the computer to:
   display a first map with the one or more areas suggested for fishing;
   receive a modification to the location, date, wind direction, water temperature, or species; and
   display a second map based on the modification.

11. The non-transitory computer-readable medium of claim 1, wherein the fishing records are stored by a cloud server associated with a cloud software service.

12. The non-transitory computer-readable medium of claim 1, wherein the one or more suggestions are expert suggestions generated by one or more experts, and wherein the instructions that cause the computer to display the suggestions on the map comprise instructions that cause the computer to display at least one credential of the one or more experts.

* * * * *